(12) United States Patent
Hogan et al.

(10) Patent No.: US 7,526,329 B2
(45) Date of Patent: Apr. 28, 2009

(54) MULTIPLE REFERENCE NON-INVASIVE ANALYSIS SYSTEM

(76) Inventors: Josh N. Hogan, 620 Kingwood Way, Los Altos, CA (US) 94022; Carol Jean Wilson, 1707 Mendenhall Dr., San Jose, CA (US) 95130

( * ) Notice: Subject to any disclaimer, the term of this patent is extended or adjusted under 35 U.S.C. 154(b) by 612 days.

(21) Appl. No.: 11/025,698

(22) Filed: Dec. 29, 2004

(65) Prior Publication Data
US 2006/0063985 A1   Mar. 23, 2006

Related U.S. Application Data

(60) Provisional application No. 60/602,913, filed on Aug. 19, 2004.

(51) Int. Cl.
*A61B 5/1455* (2006.01)
*A61B 6/00* (2006.01)

(52) U.S. Cl. .................. 600/316; 600/473; 600/476; 600/310

(58) Field of Classification Search .......... 600/310, 600/316, 473, 476, 322; 356/450, 451, 456, 356/477, 479
See application file for complete search history.

(56) References Cited

U.S. PATENT DOCUMENTS

| | | | |
|---|---|---|---|
| 5,920,390 A | * | 7/1999 | Farahi et al. ............... 356/477 |
| 6,725,073 B1 | * | 4/2004 | Motamedi et al. .......... 600/316 |
| 6,728,571 B1 | * | 4/2004 | Barbato ...................... 600/407 |

* cited by examiner

*Primary Examiner*—Eric F Winakur (57) ABSTRACT

A non-invasive imaging and analysis system suitable for measuring concentrations of specific components, such as blood glucose concentration and suitable for non-invasive analysis of defects or malignant aspects of targets such as cancer in skin or human tissue, includes an optical processing system which generates a probe and composite reference beam. The system also includes a means that applies the probe beam to the target to be analyzed and modulates at least some of the components of the composite reference beam such that signals with different frequency content are generated. The system combines a scattered portion of the probe beam and the composite beam interferometrically to simultaneously acquire information from multiple depths within a target. It further includes electronic control and processing systems.

43 Claims, 8 Drawing Sheets

MULTIPLE REFERENCE NON-INVASIVE ANALYSIS SYSTEM

CROSS REFERENCES TO RELATED APPLICATIONS

This application claims priority from U.S. provisional application Ser. No. 60/602,913 titled "Multiple reference non-invasive analysis system" filed on Aug. 19, 2004.

This application relates to U.S. utility application Ser. No. 10/949,917 filed on Sep. 25, 2004 titled "Compact non-invasive analysis system", the contents of which are incorporated by reference as if fully set forth herein. This application also relates to U.S. utility patent application Ser. No. 10/870,121 filed on Jun. 17, 2004 titled "A Non-invasive Analysis System", the contents of which are incorporated by reference as if fully set forth herein. This application also relates to U.S. utility patent Ser. No. 10/870,120 filed on Jun. 17, 2004 titled "A Real Time Imaging and Analysis System", the contents of which are incorporated by reference as if fully set forth herein.

FIELD OF THE INVENTION

The invention relates to non-invasive optical imaging and analysis and in particular to quantitative analysis of concentrations specific components or analytes in a target. Such analytes include metabolites, such as glucose. This invention also relates to non-invasive analysis of defects or malignant aspects of targets such as cancer in skin or human tissue.

BACKGROUND OF THE INVENTION

Non-invasive analysis is a valuable technique for acquiring information about systems or targets without undesirable side effects, such as damaging the target or system being analyzed. In the case of analyzing living entities, such as human tissue, undesirable side effects of invasive analysis include the risk of infection along with pain and discomfort associated with the invasive process.

In the particular case of measurement of blood glucose levels in diabetic patients, it is highly desirable to measure the blood glucose level frequently and accurately to provide appropriate treatment of the diabetic condition as absence of appropriate treatment can lead to potentially fatal health issues, including kidney failure, heart disease or stroke. A non-invasive method would avoid the pain and risk of infection and provide an opportunity for frequent or continuous measurement.

Non-invasive glucose analysis based on several techniques have been proposed. These techniques include: near infrared spectroscopy using both transmission and reflectance; spatially resolved diffuse reflectance; frequency domain reflectance; fluorescence spectroscopy; polarimetry and Raman spectroscopy.

These techniques are vulnerable to inaccuracies due to issues such as, environmental changes, presence of varying amounts of interfering contamination and skin heterogeneity. These techniques also require considerable processing to deconvolute the required measurement, typically using multivariate analysis. These techniques have heretofore produced insufficient accuracy and reliability to be clinically useful.

More recently optical coherence tomography (OCT), using a super-luminescent diode (SLD) as the optical source, has been proposed in Proceedings of SPIE, Vol. 4263, pages 83-90 (2001). The SLD output beam has a broad bandwidth and short coherence length. The technique involves splitting the output beam into a probe and reference beam. The probe beam is applied to the system to be analyzed (the target). Light scattered back from the target is combined with the reference beam to form the measurement signal.

Because of the short coherence length only light that is scattered from a depth within the target such that the total optical path lengths of the probe and reference are equal combine interferometrically. Thus the interferometric signal provides a measurement of the scattering value at a particular depth within the target. By varying the length of the reference path length, a measurement of the scattering values at various depths can be measured and thus the scattering value as a function of depth can be measured.

The correlation between blood glucose concentration and the scattering coefficient of tissue has been reported in Optics Letters, Vol. 19, No. 24, Dec. 15, 1994 pages 2062-2064. The change of the scattering coefficient correlates with the glucose concentration and therefore measuring the change of the scattering value with depth provides a measurement of the scattering coefficient which provides a measurement of the glucose concentration. Determining the glucose concentration from a change, rather than an absolute value provides insensitivity to environmental conditions.

In conventional OCT systems depth scanning is achieved by modifying the relative optical path length of the reference path and the probe path. The relative path length is modified by such techniques as electromechanical based technologies, such as galvanometers or moving coils actuators, rapid scanning optical delay lines and rotating polygons. All of these techniques involve moving parts, which have limited scan speeds and present significant alignment and associated signal to noise ratio related problems.

Motion occurring within the duration of a scan can cause significant problems in correct signal detection. If motion occurs within a scan duration, motion related artifacts will be indistinguishable from real signal information in the detected signal, leading to an inaccurate measurement. Long physical scans, for larger signal differentiation or locating reference areas, increase the severity of motion artifacts. Problematic motion can also include variation of the orientation of the target surface (skin) where small variations can have significant effects on measured scattering intensities.

Non-moving part solutions, include acousto-optic scanning, can be high speed, however such solutions are costly, bulky and have significant thermal control and associated thermal signal to noise ratio related problems.

Optical fiber based OCT systems also use piezo electric fiber stretchers. These, however, have polarization rotation related signal to noise ratio problems and also are physically bulky, are expensive, require relatively high voltage control systems and also have the motion related issues. These aspects cause conventional OCT systems to have significant undesirable signal to noise characteristics and present problems in practical implementations with sufficient accuracy, compactness and robustness for commercially viable and clinically accurate devices.

Therefore there is an unmet need for commercially viable, compact, robust, non-invasive device with sufficient accuracy, precision and repeatability to image or analyze targets or to measure analyte concentrations, and in particular to measure glucose concentration in human tissue.

SUMMARY OF THE INVENTION

The invention provides a method, apparatus and system for a non-invasive imaging and analysis suitable for measuring concentrations of specific components or analytes within a target, such as the concentration of glucose within human tissue and suitable for non-invasive analysis of defects or malignant aspects of targets such as cancer in skin or human tissue. The invention includes an optical source and an optical signal processing system which provides a probe and a composite reference beam. It also includes a means that applies the probe beam to the target to be analyzed, recombines the scattered probe beam and the composite reference beam interferometrically and concurrently acquires information from different locations within the target. It further includes electronic control and processing systems.

DETAILED DESCRIPTION OF THE INVENTION

Optical coherence tomography is based on splitting the output of a broadband optical source into a probe beam and a reference beam and of varying the optical path length of the reference beam to scan the target. This imaging and analysis technology has problems and limitations including problems and limitations related to motion occurring within the duration of a scan.

The present invention is a novel interferometric approach, which addresses these problems and limitations, by concurrently acquiring multiple meaningful interferometric signals from multiple depths within the target, thus avoiding relative motion artifacts. For purposes of this invention "concurrently acquiring" includes simultaneously acquiring and acquiring at a speed that is significantly higher than motion artifacts. Similarly "concurrent" includes "simultaneous" and "at high speed with respect to motion artifacts" and "concurrently" includes "simultaneously" and "at high speed with respect to motion artifacts". With the present invention the interferometric information from the different depths within the target can be distinguished from each other and separated by electronic processing.

The invention involves generating a composite reference beam consisting of multiple beams (or component reference beams) each corresponding to a different path length. In addition to corresponding to different path lengths, at least some components of the composite reference beam are also modulated in a different manner to allow the interferometric information corresponding to different component reference beams to be separated by electronic processing. This enables a compact imaging and analysis system which can concurrently acquire and analyze information from different depths within a target and thereby avoid undesirable motion related artifacts.

A preferred embodiment of this invention is illustrated in and described with reference to FIG. 1 where a non-invasive optical analysis system is shown. The analysis system includes an optical processing system that generates a probe beam and a reference beam from a broadband optical source 101, such as a super-luminescent diode or a mode-locked laser, whose collimated output 102, consists of a broad band, discrete or continuous, set of wavelengths.

The output beam 102, is passed through a beam splitter 103, to form a probe beam 104 and a reference beam 105 (which also becomes the composite reference beam on its return path). The probe beam 104 passes through an optional focusing lens 106. The focusing probe beam 108 is directed by an optional angled mirror 109 and applied to the target 110 below the angled mirror.

At least part of the radiation of the beam applied to the target is scattered back and captured by the lens 106 to form captured scattered probe radiation. Scattering occurs because of discontinuities, such as changes of refractive index or changes in reflective properties, in the target. The captured scattered probe radiation passes through the lens 106 back to the beam splitter 103.

The reference beam 105 is applied to a second beam splitter 111 where it is separated into multiple component reference beams (in this embodiment two component reference beams), one of which 112 is referred to as reference A and the other 113 referred to as reference B. The two reference beams 112 and 113 are reflected by reflective elements 114 and 115 respectively which in this embodiment are modulating reflective elements (typically substantially fully reflective elements).

By having the optical path lengths to the two component reference beams 112 and 113 different from each other, interferometric information can be detected which relates to depths within the target separated by the optical path length difference. The actual depths correspond to the total optical path lengths of the composite reference beam 105 and the separate component reference beams 112 and 113.

The reflective elements 114 and 115 include modulating elements and are also referred to as modulating reflective elements. The modulating reflective elements modulate the two reference beams 112 and 113 at different frequencies. This causes the interferometric information from two different depths (within the target) to have different frequency components which allows the interferometric information from the two different depths to be separated by electronic filtering. This provides a mechanism for concurrently analyzing information from different depths within the target, thereby avoiding motion artifacts.

At least a part of the two modulated reflected component reference beams are re-combined by the beam splitter 111 to form a re-combined reference beam which returns along the path of the reference beam 105 and is referred to as a composite reference beam. The reflected re-combined reference beam, or composite reference beam, is combined interferometrically with the captured scattered probe radiation in the beam splitter 103. (Although typically referred to as a beam splitter the optical element 103 also operates as an optical combining element, in that it is in this element that reflected re-combined reference beam and captured scattered probe radiation combine interferometrically.) The resulting composite interference signal 107 is detected by the opto-electronic detector 116 to form a composite electronic signal.

A meaningful interferometric signal only occurs with interaction between the reference beam and light scattered from a distance within the target such that the total optical path lengths of both reference and probe paths are equal or equal within the coherence length of the optical beam. In this preferred embodiment concurrent information from two different depth locations is acquired and analyzed.

The preferred embodiment also includes an electronic processing module, 117, which interacts with an electronic control module 119 by means of electronic signals 118. The control module 119 provides timing signals, included in signals 118, to provide the electronic processing module 117 with timing signals to assist the processing module with filtering and processing the detected composite interferometric signals. The control module 119 also generates control and drive signals for the system, including signals 120 to control and drive the optical source and signals 121 and 122 which modulate the modulating reflective elements 114 and 115 respectively.

Modulation can be accomplished by phase modulating the component reference beams 112 and 113 by means of the modulating reflective elements 114 and 115, which in this case would be reflective phase modulators. Applying a repetitive phase modulation of nominal magnitude 90 degrees in single pass, (180 degrees double pass) or greater generates a detectable interferometric signal related to the frequency of the repetitive phase modulation.

An advantage of phase modulation is that phase modulators can operate at very high frequencies. This enables having the two modulating reflective elements 114 and 115 modulate at frequencies that are substantially different in frequency from each other. This reduces crosstalk between the two signals and simplifies separating the composite electronic signal into two component electronic signals by electronic filtering. The component electronic signals provide concurrent information relating to different depth locations within the target.

Figure 2A:
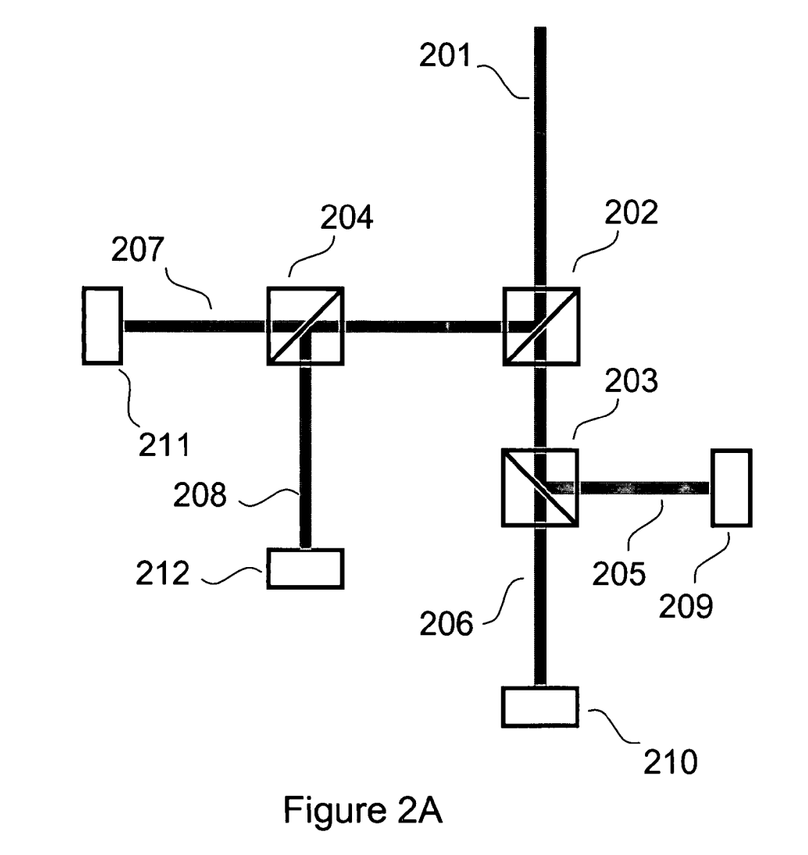
FIG. 2A is an illustration of a design with up to four modulating reflective elements.

High frequency modulation is also facilitates having more than two component reference paths. An example of a multiple reference path design with up to four different component reference path lengths is illustrated in FIG. 2A, where the reference beam 201 is applied to three beam-splitters 202, 203 and 204. The four separated component reference beams 205, 206, 207 and 208 are reflected by modulating reflection elements 209, 210, 211 and 212.

The total optical path lengths of each of the four component reference beams can be configured to provide a composite interferometric signal from four different depths within the target. By modulating the four modulating reflection elements 209, 210, 211 and 212 at different frequencies, concurrent information from up to four depth locations can be separated by filtering in the electronic domain.

In an alternative embodiment, rather than phase modulating, the modulating reflective elements involve length modifying devices, such as piezo-electric devices. By modifying the length of each reference path at different frequencies, (or by having different magnitude of length modifications, or by a combination of different frequencies and different length modifications), the information relating to the different component reference signals can have different frequency content and can be separated by filtering in the electronic domain.

Piezo-electric devices with dimensions of the order of several milli-meters can produce translations of the order of microns at relatively high frequencies, especially when operated in resonant mode. This enables implementing multiple modulated component references at different frequencies in a compact manner.

Optical processing systems, such as described above, can be fabricated on a compact micro-bench, such as a silicon micro-bench. This is illustrated in FIG. 1 by the boundary or box 123 which illustrates the boundary of a rigid micro-bench. All components within the boundary or box 123 can be mounted on such a micro-bench. By varying the distance between the micro-bench 123 and the optional angled mirror 109, the distance into the target from which the meaningful interferometric signals originate is varied along a line determined by the angled mirror. Various methods of translating the micro-bench are illustrated and described in the patent application Ser. No. 10/949,917 referenced by and incorporated into this application.

This provides a method of concurrently obtaining interferometric information from different depths within the target (by means of the multiple component references) and also of varying the locations within the target from which this concurrent set of information originates. This provides a method of obtaining multiple sets of information that are insensitive to motion and in a manner that allows the information to be separated by electronic filtering or processing.

In an alternative embodiment using two piezo-electric length adjusting devices, the two piezo-electric devices can be modulated at the same frequency but designed to produce path length changes of significantly different magnitudes. This results in interferometric signals with correspondingly significantly different frequencies. Because multiple resultant interferometric information exists within the same interferometric signal, an interferometric signal may include more than one interferometric signals. For purposes of this application interferometric signal, composite interferometric signal and interferometric signals may be used interchangeably. Also while "beam" is often used to indicate well controlled radiation as opposed to scattered or diffuse radiation, for purposes of this application beam and radiation may be used interchangeably.

Figure 3:
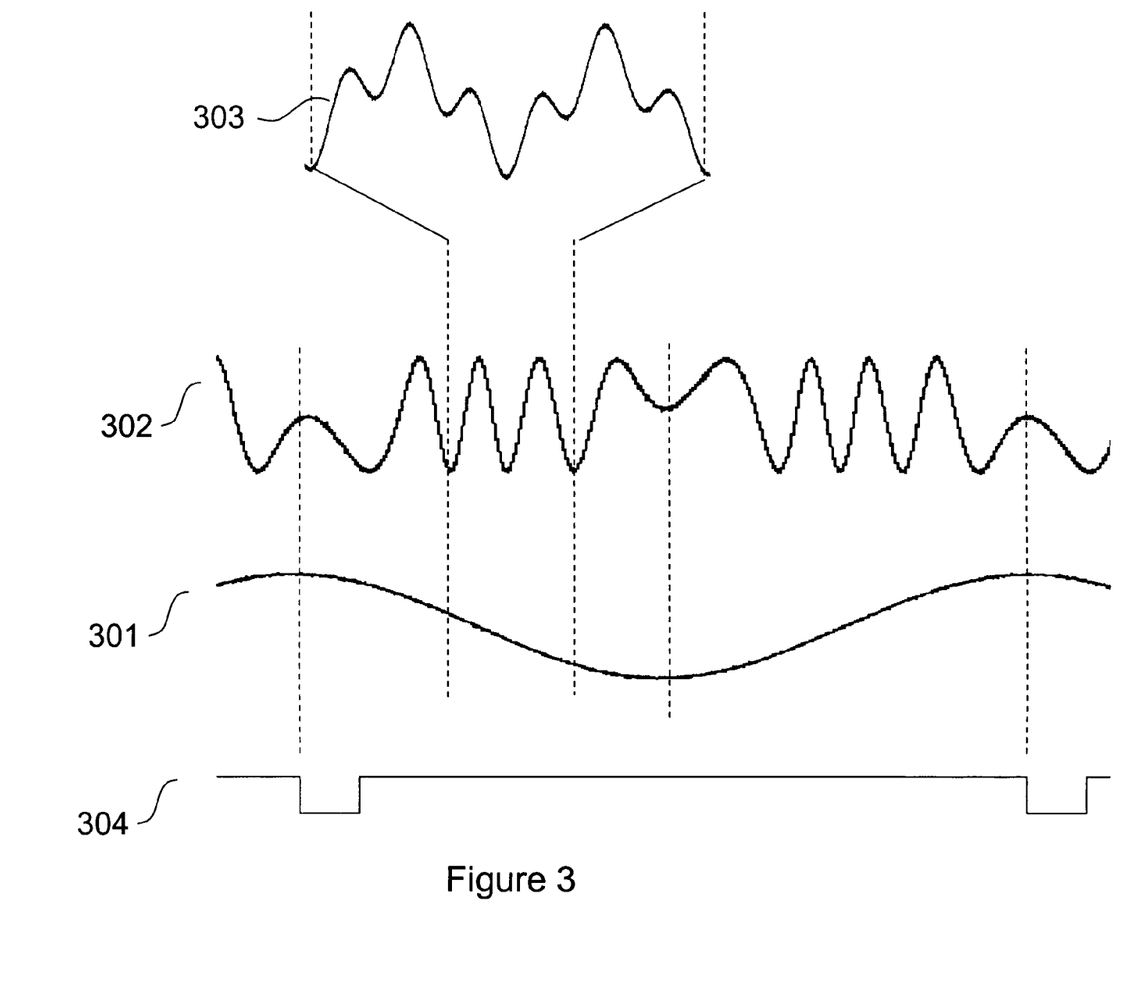
FIG. 3 illustrates timing, drive and different frequency content signals.

A suitable drive signal for the piezo devices is illustrated FIG. 3 where a sine wave 301 is shown. By applying drive signals with the same frequency but different amplitudes (or by using piezo-devices with different responses) different periodic path length changes can be achieved, resulting in different interferometric signal frequency content. The electronic signal resulting from a single interference signal is illustrated by the signal 302. An example of several cycles of a composite electronic signal resulting from detecting a composite interferometric signal, from a system with two component reference beams, is illustrated by signal 303.

The composite signal 303 is composed of two components, one with being two cycles at a lower frequency and the other being six cycles at three times the nominal frequency of the first component. The signal 303 is located at a reasonably linear portion of the drive sine wave. The signal 304 indicates the repetitive period of the drive and interferometric signals.

The interferometric signals 302 and 303 have nominally fixed frequency content at the linear portion of the drive sine wave and a decreasing frequency content as the extremes of the drive sine wave are approached, as illustrated by signal 302. The frequency content may also be non-linear due to non-linear response of the piezo (or phase modulating) device. Non-linear aspects may be compensated for by conventional calibration techniques. The fixed frequency content (during the linear portion of the drive signal or when compensated) due to different component reference signals can be readily separated out from the detected composite electronic signal by means of electronic filtering or by digital signal processing.

Separation by means of electronic filtering can be accomplished by digitizing the detected composite electronic signal and subsequent digital signal processing to separate out the component electronic signals. Alternatively, analog electronic preprocessing using analog filtering and pre-amplification or various combinations of analog processing and digital processing can be used. Gating signals related to the repetitive drive signals can also be used to selectively process fixed frequency components of signals.

The ability to separate the information from different interferometric signals can be enhanced by other means. For example, ensuring there is a harmonic relationship between aspects of the various interferometric signals facilitates separating out the information related to different references. A harmonic relationship between aspects includes, but is not limited to, having the frequency of the linear portion of one interferometric signal an integral number of times the frequency of a second interferometric signal and preferably with a known phase relationship between them. A harmonic relationship facilitates separating the information by means of a processing algorithm. This allows independent measurements to be made in as little as a half cycle of the lower frequency, which allows more numerous independent measurements to be made, thereby further increasing insensitivity to motion artifacts.

Figure 1:
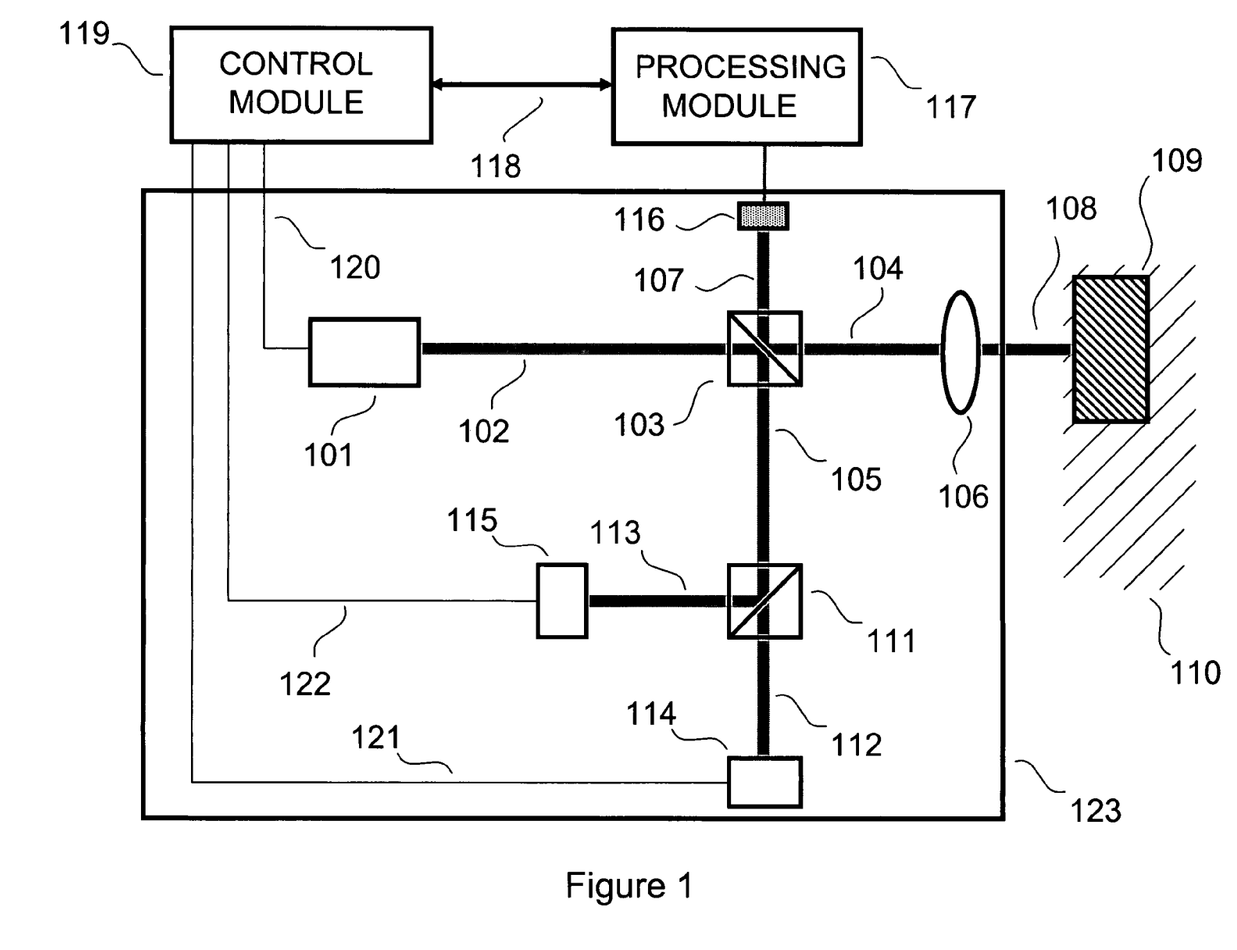
FIG. 1 is an illustration of the non-invasive analysis system according to the invention.
Figure 4:
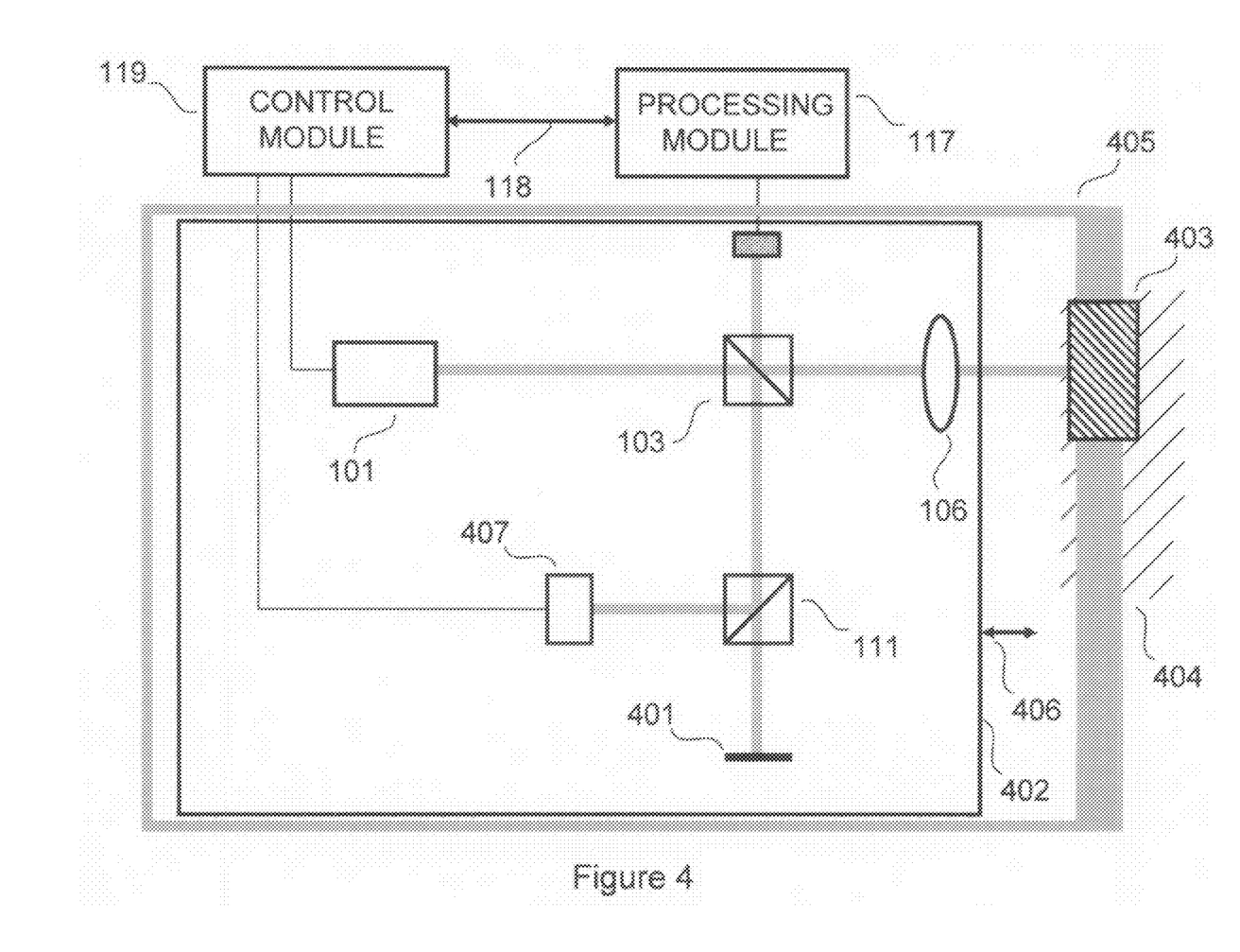
FIG. 4 is an illustration of an another embodiment of the invention.

Another embodiment is illustrated in FIG. 4 which in some respects is similar to the embodiment illustrated in FIG. 1. In the embodiment of FIG. 4 the reflective element 401 does not contain a modulator. The interferometric signal corresponding to this component reference beam is generated by translating the optical system 402 (enclosed in the box labeled 402). This optical system is repetitively translated toward and away from the turning mirror 403 which directs the probe beam or radiation in and out of the target 404.

This translation of the optical system 402 with respect the turning mirror 403 can be accomplished by conventional means, such as, enclosing the optical system 402 within a frame 405 that holds the turning mirror and allows translational motion within the frame. The translational motion, indicated by 406, can be accomplished by conventional means such as electro-mechanical or piezo-electric means. The speed of this translation determines the frequency of the interferometric signal associated with the reflective element 401.

The second reflective element 407 is a modulating reflective element similar to those described in other embodiments. The interferometric signal associated with this modulating reflective element 407 has frequency components that are determined by a combination of the modulating frequency and the translation speed of the optical system 402. By selecting a modulating frequency that gives an interferometric signal with a substantially different frequency to that due to the translational speed, the interferometric information related to this modulating reflective element can be separated from information related to the reflective element 401.

Figure 5:
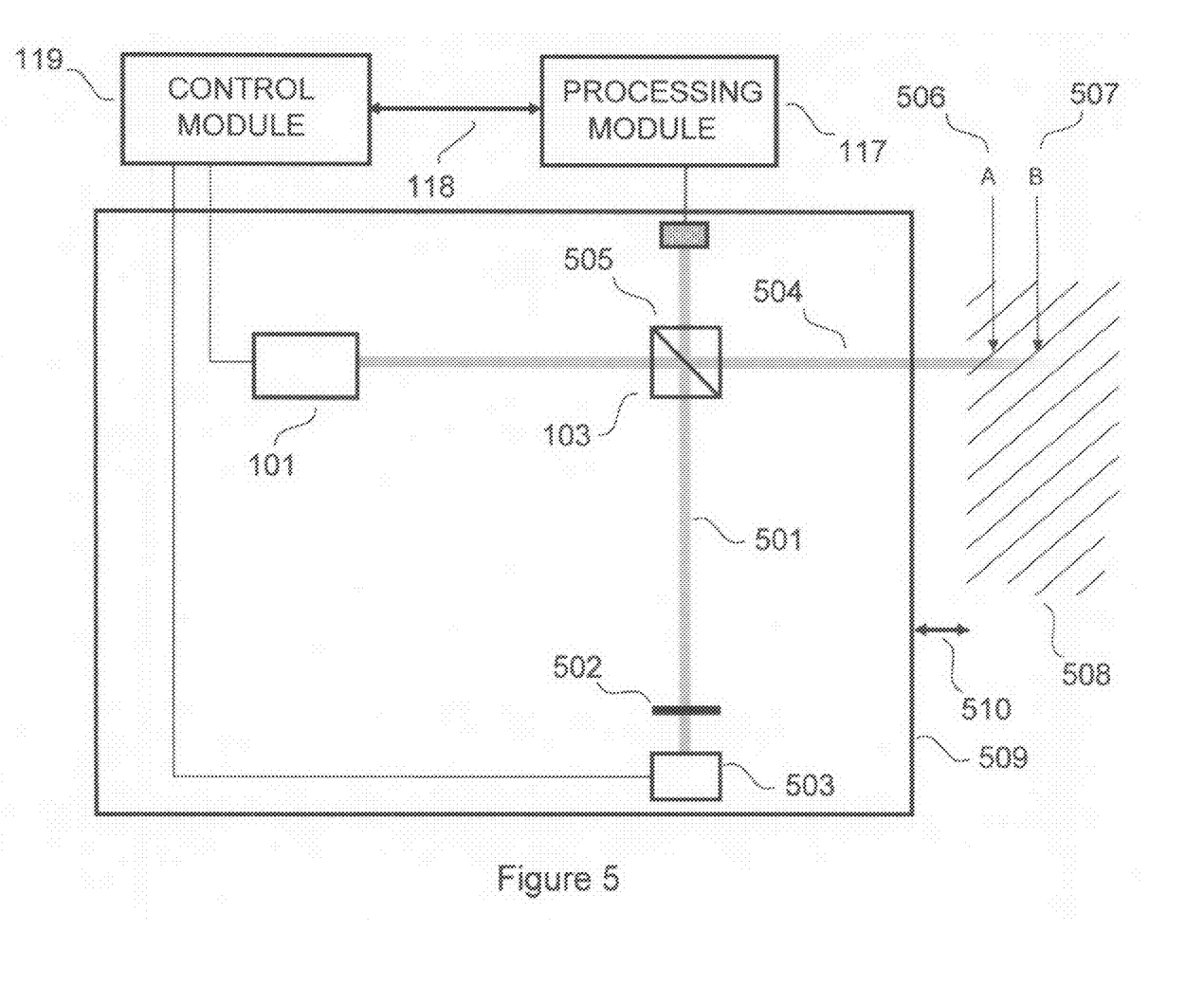
FIG. 5 is an illustration of an embodiment involving a polarization reflective element.

Another embodiment is illustrated in FIG. 5 where the reference beam 501 is partially reflected by a polarization sensitive mirror 502. The polarization sensitive mirror 502 reflects radiation at one polarization and transmits radiation at the opposite polarization. The transmitted radiation is reflected by the modulating reflective element 503 and is re-transmitted through the polarization sensitive mirror 502 to form the composite reference beam 501.

The composite reference beam 501 is combined with the captured scattered probe radiation 504 in the beam splitter 505 (acting as a beam combiner). Meaningful interference signals are concurrently acquired from two depths 506 and 507 within the target 508 (indicated by the arrows labeled A and B) corresponding to the component reference reflective elements 502 and 503.

The frequency content of the interference signal corresponding to the polarization sensitive reflective element 502 is determined by the speed with which the micro-bench 509 is translated back and forth in the direction indicated by 510. The frequency content of the interference signal corresponding to the modulating reflective element 503 is determined by the modulating characteristics and the speed at which the micro-bench is translated. The modulating frequency can be selected to ensure the frequency content of the two interferometric signals are significantly different and therefore can be separated by electronic filtering.

Figure 6:
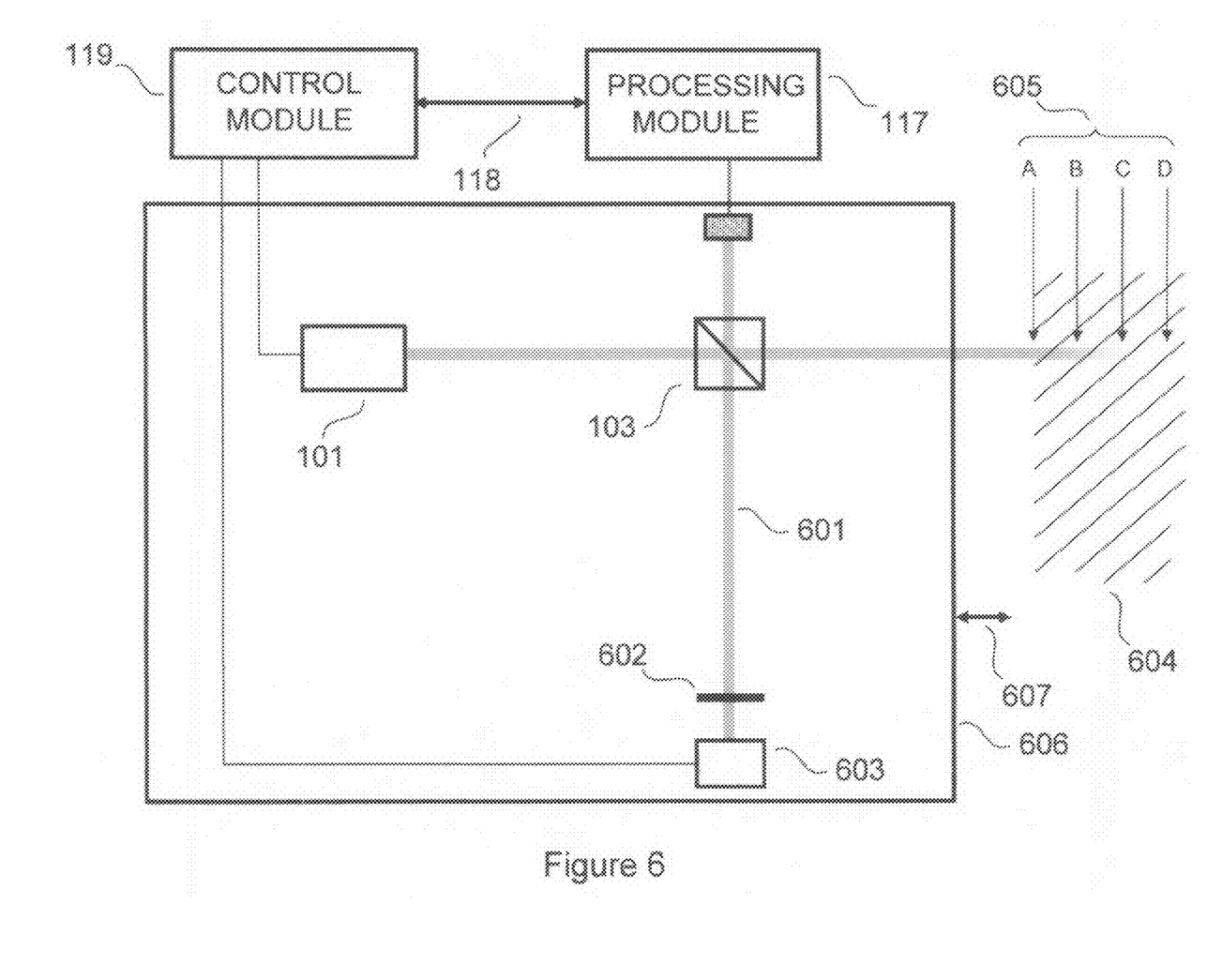
FIG. 6 is an illustration of an embodiment involving a partially reflective element.

Yet another embodiment is illustrated in FIG. 6 where the reference beam is partially reflected by the partial reflective element 602. A portion of the reference beam is also transmitted through the partial reflective element 602 which is then reflected by the modulating reflective element 603, which is typically a substantially fully reflective element, to form a once modulated reference beam. A portion of the once modulated reference beam is transmitted through the partial reflective element 602 to form a component of the composite reference beam 601.

A portion of the once modulated reference beam is also reflected by the partial reflective element 602 and is again reflected and further modulated by the modulating reflective element 603. A portion of this twice modulated reference beam is then transmitted through the partial reflective element 602 to form another component of the composite reference beam 601 and a portion also reflected by the partial reflective element 602 to form further components of the composite reference beam that are multiple times modulated reference beams. In this embodiment the component reference beams are not separated into different physical paths, but rather the different components are delayed in time along the same path. For purposes of this invention, separating the reference beam into multiple component reference beams includes, but is not limited to, this method of temporal separation as well as physical path separation.

In this manner a composite reference beam 601 is generated that has multiple interferometrically significant components that correspond to depth locations within the target 604 a subset of which depths are indicated by the set of arrows 605 labeled B, C and D. The depth location indicated by the arrow labeled "A" corresponds to the partially reflective element 602 and would have a corresponding interference signal with a frequency content determined by the relative motion between the target 604 and the micro-bench 606 along the direction indicated by 607. This could be zero in the case where there is no relative motion between the target and micro-bench.

Depth location "B" corresponds to the modulating reflective element 603 and would have a corresponding interference signal with a frequency content determined by the modulating frequency. Depth location "C" corresponds to a double pass between the modulating reflective element 603 and the partially reflective element 602 and would have a corresponding interference signal with a frequency content twice that of the interference signal corresponding to depth location "B".

Depth location "D" corresponds to a triple pass between the modulating reflective element 603 and the partially reflective element 602 and would have a corresponding interference signal with a frequency content three times that of the interference signal corresponding to depth location "B". Interference signals corresponding to higher order multiple passes with correspondingly higher frequencies could also exist. In general the resulting composite interference signal will have multiple interference components which contain concurrent information from multiple depth locations.

There is a decrease in the intensity of the reference beam components corresponding to higher order multiple passes. The amount of this decrease in intensity depends on the partially reflective element. For example, if the partial reflective element reflects 50% and transmits 50% of the reference beam, then the reference beam component from the partially reflective element 602 (corresponding to A) will have a relative intensity of 50%; the reference beam component from a single pass to the modulating reflective element 603 (corresponding to B) will have a relative intensity of 25%.

Similarly the reference beam component from a double pass to the modulating reflective element 603 (corresponding to C) will have a relative intensity of 12.5%; the reference beam component from a triple pass to the modulating reflective element 603 (corresponding to D) will have a relative intensity of 6.25%; and so on. Typically the captured scattered signal from the target will be of low intensity and having reference beam components with different relative intensities will not be significant as they will likely exceed the intensity of the scattered signal. In the many possible variations of this embodiment the reference beam is separated into component reference beams and at least a portion of the component reference beams are re-combined into the composite reference beam by the combination of at least one partially reflective element and at least one substantially fully reflective element.

Figure 7:
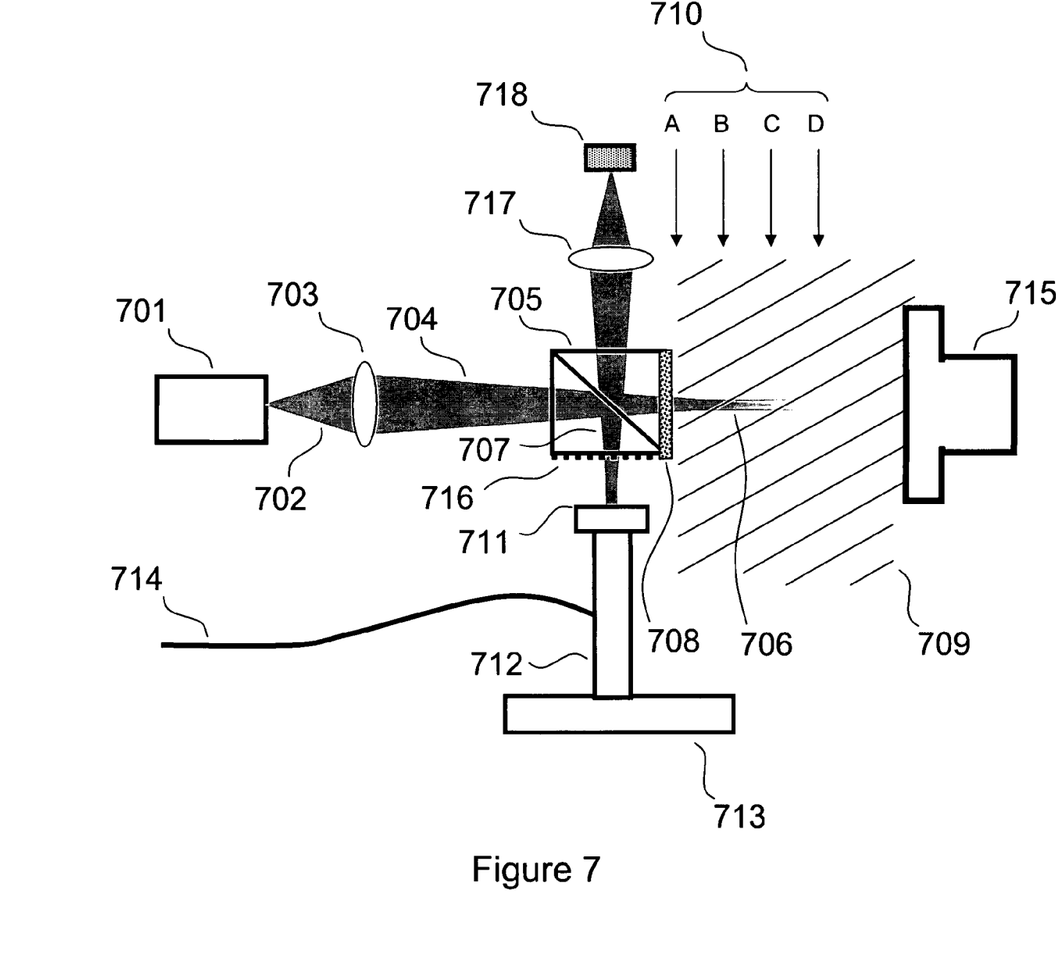
FIG. 7 is an illustration of another embodiment involving a partially reflective element.

Yet another preferred embodiment of the optical processing system is illustrated in FIG. 7 where the optical source 701, such as a super-luminescent diode or a mode locked laser, whose output beam 702 consists of a broad band, discrete or continuous, set of wavelengths. The output beam is focused by a focusing element 703 which may be a single lens or a more complex optical system. The focusing beam 704 is passed through a beam splitter 705 to form a probe beam 706 and a reference beam 707. The probe beam 706 passes through an optional index matching layer 708 and is applied to the target to be analyzed 709. The index matching layer 708 is selected to reduce the index mis-match between the beam-splitter 705 and the target to be analyzed 709.

At least part of the probe beam applied to the target is scattered back and captured to form captured scattered probe radiation. Scattering occurs because of discontinuities, such as changes of refractive index or changes in reflective properties, in the target. The captured scattered probe radiation is applied to the beam splitter 705 where it is interferometrically combined with the composite reference beam 707 (on its return path).

A surface 716 (indicated by the dashed lines) of the beam-splitter 705 is partially reflective. The reflected portion forms a component of the composite reference beam and generates a meaningful interference signal by interferometrically combining with the portion of the captured scattered probe radiation that originates from the region of the target 709 indicated by the arrow labeled "A" of the set of arrows 710.

The portion of the reference beam 707 transmitted through the partially reflective surface 716 of the beam-splitter 705 is reflected back to the partially reflective surface by the modulating reflective element 711. The portion of this single pass once modulated reflected beam that is transmitted through partially reflective surface 716 becomes another component of the composite reference beam 707.

As described before, multiple pass reflections between the partially reflective surface 716 and the modulating reflective element 711 generate multiple components of the composite reference beam 707 and will generate meaningful interference signals when combined with captured scattered probe radiation originating at regions within the target 709 a subset of which are indicated by the arrows labeled "B", "C" and "D". The multiple component reference beams, including that first reflected by the partially reflective element 716 are all re-combined to form the composite reference beam 707.

The composite reference beam 707 is combined with the captured scattered probe radiation and the resulting composite interference signal is focused by the lens 717 onto the opto-electronic detector 718 to generate a composite electronic signal. The composite electronic signal can be separated into component electronic signals containing concurrent information from multiple depth locations which can then be processed and analyzed.

The locations of the regions within the target 709 labeled A,B,C and D are determined by the location of the partially reflective surface 716 and the distance between the partially reflective surface 716 and the modulating reflective element 711 (adjusted by relative refractive index values). Meaningful interferometric signals will also be generated corresponding to other depths within the target at integral numbers times the distance between the arrows in the set of arrows 710. Typically the intensity of scattered signals diminish significantly with increasing depth. Also the intensity of the reference components diminish with multiple reflection passes between the partially reflective surface 716 and the modulating reflective element 711.

The frequency components of the interference signals generated by the different components of the composite reference beam are all different and, with the exception of that corresponding to region "A", are (substantially) determined by the modulating frequency of the modulating reflective element. For example, if the signal corresponding the region "B" were 20KHz, then that of region "C" would be 40KHz and that of region "D" would be 60KHz and so on with higher frequencies for deeper regions. An advantage of this embodiment is that the frequencies of the different component interference signals are automatically harmonically related or have aspects that are harmonically related.

While the modulating reflective element could be a reflective phase modulator, in this preferred embodiment the modulating reflective element is modulated by means of a piezo electric device 712 which is rigidly secured at one end to a portion 713 of the micro-bench or its housing. The modulating reflective element is attached to the other end. Applying a modulating voltage by means of a conventional electrical connection 714 modulates the reference beam.

The frequency of the resulting interference signal at "B" is determined by the frequency of the modulating voltage and the displacement of the piezo. The piezo device may be operated in resonant mode at a high frequency modulating voltage. The displacement may be small compared to the coherence length of the optical source.

The interference signal corresponding to region "A" in the target 709 is determined by the relative motion between the target 709 and the beam-splitter 707 containing the partially reflective surface 716. This relative motion may be negligible in the case of a stationary target. Alternatively the target may be vibrated in a controlled manner. In this preferred embodiment a vibration is applied to the target by means of an oscillating or vibrating device 715 that is applied to opposite side of the target from the beam-splitter 705. A flexible or deformable index matching layer 708 can facilitate having the surface region "A" of the target vibrate.

Many alternative methods of imposing an oscillating relative motion between the target and the beam-splitter. For example the vibrating element could be an annular design surrounding the beam splitter 705 and on the same side of the target as the beam-splitter 705. A conventional voice coil or a piezo device could be used to impart a small vibration. The frequency and amplitude of the vibration can be selected so that the resulting interference signal corresponding to region "A" does not significantly interfere with the frequency of the interference signals corresponding to other regions including regions B, C and D etc.

Figure 8:
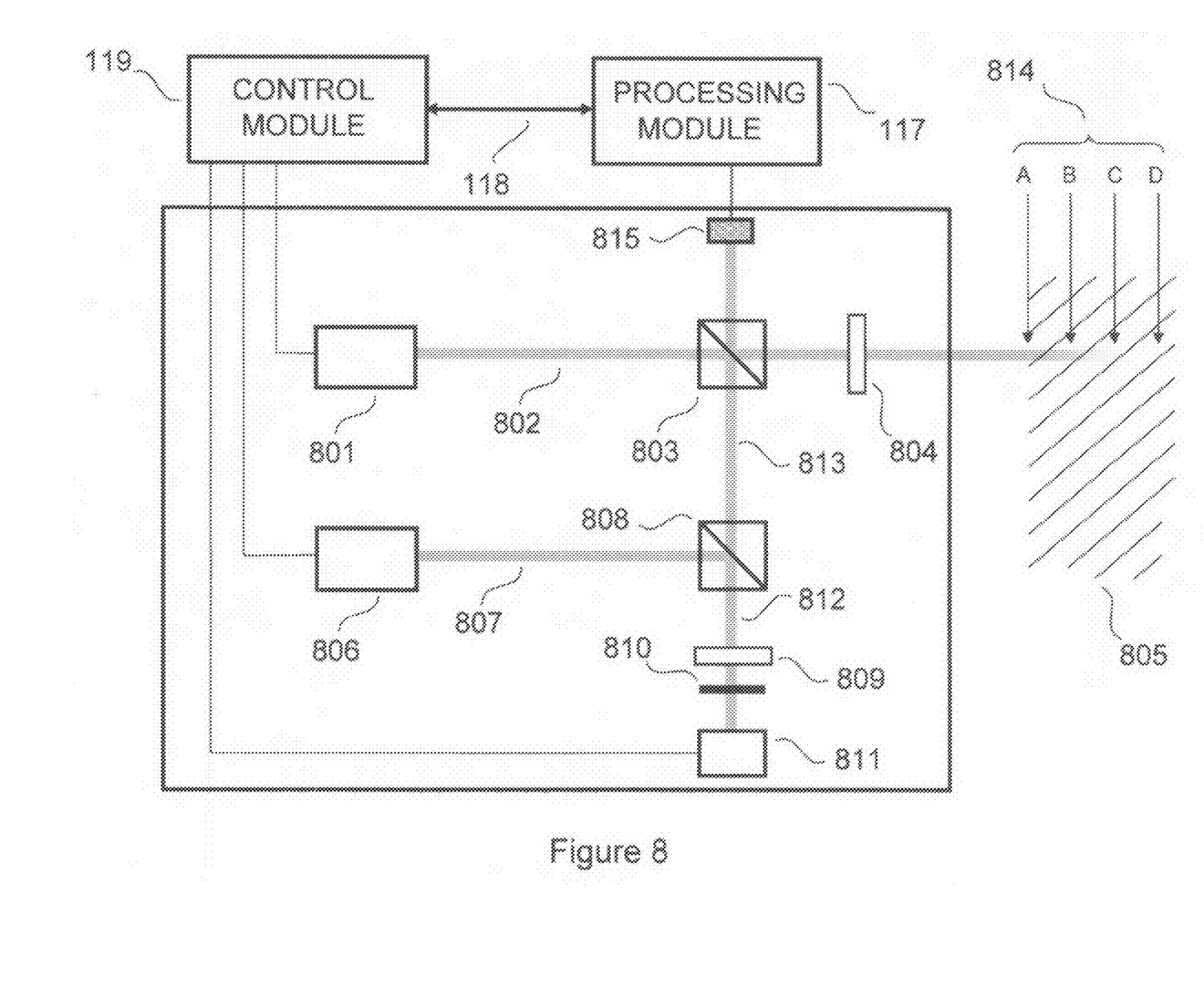
FIG. 8 is an illustration of another embodiment involving two separate optical sources.

Yet another embodiment is illustrated in FIG. 8 employing two mode-locked laser sources. A first mode-locked laser source 801 generates a collimated probe beam 802 which is passed through a first polarization beam-splitter 803 and a first quarter wave plate 804 and is applied to the target 805. A portion of the scattered probe beam from the target passes back through the quarter wave plate 804 to the polarization beam-splitter 803 to form the captured scattered probe radiation.

A second mode-locked laser source 806 generates a collimated reference beam 807 which is applied to a second polarization beam-splitter 808 which directs the reference beam through a second quarter wave plate 809 to a partially reflective element 810 and a modulating reflective element 811, which, as described previously, generates an initial composite reference beam 812.

At least a portion of the initial composite reference beam 812 passes through the beam-splitter 803 to form the composite reference beam 813 which is interferometrically combined with the captured scattered probe radiation in the first beam-splitter 803 where it forms a composite interference signal which contains concurrent information from multiple depth locations, a subset of which at a particular time are indicated by the arrow set 814. The composite interference signal is detected by the opto-electronic detector 815 and the detected composite electronic signal processed as described previously.

By controlling the phase relationships between the two mode-locked lasers 801 and 806 the specific locations of the arrows in the set of arrows 814 within the target 805 can be varied, as described in the related U.S. patent application Ser. Nos. 10/870,120 and 10/870,121 incorporated herein by reference. This provides a motion insensitive method of analyzing or imaging targets by concurrently acquiring a set of information from multiple depth locations within a target and varying or scanning the locations of the set.

As described earlier, gating signals can be employed to selectively process the detected interference signal at specific times within the modulating drive signal. The timing of the gating signals, with respect to the modulator drive signal, can be selected to optimize distinguishing and separating the information from the multiple interference signals. In this manner a composite interference signal containing concurrent information from multiple depth locations within the target can be acquired, and the concurrent information can be separated and processed.

Since the information content contained in each component of the composite interference signal has a different frequency content, they can be separated out by electronic filtering. The ability to separate by filtering can be enhanced by means of adaptive filter parameters that dynamically change with the characteristics of the modulating drive signal. Furthermore the target can be systematically scanned in depth by translating the micro-bench on which the optical system is fabricated while keeping constant the nominal distance between the multiple regions being concurrently analyzed or as described in the embodiment of FIG. 8.

Concurrently obtaining information from different depths with in the target provides the ability to measure and analyze characteristics of the target in a manner that is insensitive to relative motion between the target and the analyzing system. For example, a target where the scattering intensity decreases in a known manner that can be transformed to a linear relationship with depth allows scattering information to be measured by concurrently measuring the intensity of the captured scattered probe radiation at two or more depths within the target.

Analyzing scattering information of targets can provide information relating to the concentration of components within the target. For example, the scattering coefficient of tissue can be analyzed to determine the concentration of components or analytes, such as glucose, within the tissue.

Because each set of concurrent measurements is insensitive to motion, the ability to acquire numerous sets of concurrent measurements at various depths within the target enables averaging of the results in a manner that is also insensitive to motion. Concurrently obtaining information from multiple different depths within the target, by means of multiple different reflective elements or multiple passes to a reflective element, provides the ability to process the information related to different depths to provide imaging information regarding the target. This can provide imaging information with increased insensitivity to motion.

For example, in FIG. 4, where two reflective elements are illustrated, by having the path lengths of the reflective elements offset by half the magnitude of the scan 406, a scan of the magnitude indicated by 406 can be accomplished twice as fast (by actually only translating half the indicated distance) as with a single reflective element, thereby increasing insensitivity to motion by a factor of two. Similarly, increasing the number of evenly spaced reflective elements to 4, 8, 16, etc. increases the insensitivity to motion by a corresponding factor of 4, 8, 16, etc.

The configuration illustrated in FIG. 7 can also be used to increase insensitivity to motion by acquiring multiple sets of information concurrently. Many variations of the relationship between the magnitude of the scan and the selection of depth locations from which concurrently acquired information is acquired. Specific configurations can be designed to suit specific applications.

It is understood that the above description is intended to be illustrative and not restrictive. Many of the features have functional equivalents that are intended to be included in the invention as being taught.

Many variations and combinations of the above embodiments are possible, for example, various combinations of modulators can be used, including but not limited to phase modulators and piezo-electric modulators. Mechanically amplified piezo-electric actuators can be used to increase length changes or to translate the optical system on a microbench. In some embodiments the relative optical path lengths of reference beams could be systematically varied to vary the relative locations from which information is obtained concurrently.

The drive signals to modulators do not need to be sine waves, but could be other generated waveforms that, for example, extend the linear duration of the scan. Extending the linear portion of the modulator drive signals enhances the ability to separate frequency content by electronic filtering. The ability to separate by filtering can also be enhanced by means of adaptive filter parameters that dynamically change with the characteristics of the modulating drive signal. This adaptive approach facilitates the use of the most readily generated modulating drive signals, including but not limited to, sine waves. The number of reflective elements does not need to be a number that is a power of 2. Other modulators, including but not limited to acousto-optic modulators using transducers could be used. The polarization sensitive reflective element of 502 of FIG. 5, or the partially reflective element 602 of FIG. 6 could also be translated by a piezo electric device to impose or modify the frequency content of the associated interference signals. The embodiment illustrated in FIG. 7 could utilize a collimated beam, rather than a focusing beam. The quarter wave plates 804 or 809 of FIG. 8 could be replaced with other polarization components or polarization components could be added to embodiments to enable analyzing polarization rotation by analytes in the target.

The preferred embodiments that are illustrated are free space configurations. Equivalent configurations could also be implemented in optical fiber or in combinations of free space and optical fiber. In such designs or configurations beam splitters could be replaced by fiber couplers. Mirrors could be replaced by fiber reflective elements, such as fiber loops or Bragg gratings. Also, while the preferred embodiment illustrated glucose measurement according to the present invention, the invention provides a general capability of non-invasive imaging and analysis of characteristics of interest in targets under analysis. While many techniques for separating and re-combining reference beams may be used, typically at least part of some of the multiple component reference beams are re-combined by at least some of the elements that separated the multiple component reference beams, so as to form the composite reference beam.

Figure 2B:
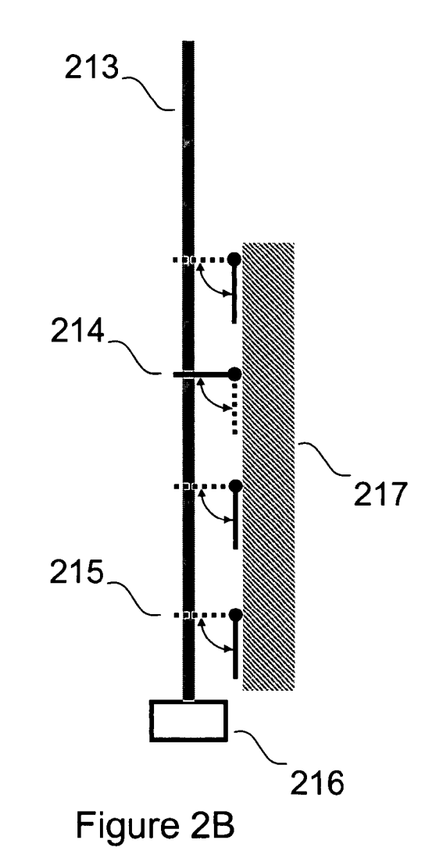
FIG. 2B is an illustration of a design using a MEMS device.

Other techniques for separating the reference beam into component reference beams can be employed. For example, a MEMS (Micro-Electro-Mechanical System) mirror array could be used. An example of an embodiment using a MEMS mirror array is illustrated in FIG. 2B where the reference beam 213 is routed through a set of switchable micro mirrors, one of which 214 is shown in a position to reflect all or part of the reference beam 213. Other switchable micro mirrors, such as 215 are shown in a non reflecting position. An optional modulating reflective element 216 can provide a component of the composite reference signal.

Individual micro mirrors, such as 214 or 215 can be rapidly switched in and out of the reference beam. The speed with which the micro mirrors come into the reflective position can be used to determine the frequency content of the resulting interferometric signal or the micro-mirror array unit 217 could be translated to generate a specific frequency content. An effective long physical scan can be accomplished by switching into reflective positions micro mirrors that have a large physical separation, thus avoiding the requirement of a long physical scan.

Many configurations are possible, for example, switching of widely separated mirrors can be done concurrently but at different speeds to allow the resulting interferometric signals to be separable in the electronic domain, or switching can occur one mirror at a time and the signal used in conjunction with the signal simultaneously available from the modulating reflective element 216 to determine relative depth information, or in yet another configuration, switching could occur one mirror at a time but at high speed (concurrently) and with sequentially switched mirrors having a large physical separation, thus avoiding motion artifacts.

The resulting composite reference signal generates interference signals when combined with the captured scattered probe radiation. The resulting interference signals can be separated in the electronic domain by digital electronic processing involving various combinations of high speed sequential signal sampling in the time domain and electronic filtering. Many variations involving different beam separation and modulation configurations are possible, for example the beam splitter separation method of FIG. 2A could be combined with the mirror array of FIG. 2B. One such configuration would be to use a beam-splitter to separate and direct one portion of the reference beam to a modulating reflective element and a second portion to the micro-mirror array.

The preferred embodiments are described and illustrated in terms of an optical processing system generating broadband optical probe and reference beams (or radiation), however the invention is not limited to optical radiation. The invention applies to all regions of the electromagnetic spectrum, including but not limited to, micro-wave or X-ray, and is not restricted to the region conventionally referred to as optical. The invention applies to other forms of radiation, including but not limited to acoustic radiation.

For example, an ultra-sound source of acoustic radiation with a broad spectral range could be used to generate the probe and reference beams (or radiation). Acoustic reflective elements and length modulators or acoustic modulating techniques could be used to generate the composite reference beam along other acoustic elements including but not limited to acoustic lenses. The resulting ultra-sound system would constitute a non-invasive imaging and analysis system according to the invention.

For purposes of this invention a source of broadband radiation, includes but is not limited to, optical sources of, such as SLDs, mode-locked laser, LEDs, other regions of the electromagnetic spectrum and sources of acoustic radiation.

Many of the features have functional equivalents that are intended to be included in the invention as taught. For example, the optical source could include multiple SLDs with either over-lapping or non-overlapping wavelength ranges, or, in the case of a mode-locked laser source could be an optically pumped mode-locked laser, it could be a solid state laser, such as a Cr:LiSAF laser optically pumped by a diode laser.

The optical source could be an actively mode-locked laser diode or a passively mode locked by a Kerr lens or a semiconductor saturable absorber mirror. Gain switched optical sources, with optical feedback to lock modes may also be used. For purposes of this invention, mode-locked lasers will include gain switched optical sources. The optical source could be a VCSEL (vertical cavity surface emitting laser), or an LED (light emitting diode) or an incandescent or fluorescent light source or could be arrays of the above sources.

Other examples will be apparent to persons skilled in the art. The scope of this invention should be determined with reference to the specification, the drawings, the appended claims, along with the full scope of equivalents as applied thereto.

What is claimed is:

1. A method for non-invasive analysis of a target comprising:
    generating a probe beam and a reference beam;
    separating the reference beam into multiple component reference beams;
    modulating at least some of the multiple component reference beams;
    re-combining, by at least some of the elements that separated said multiple component reference beams, at least part of some of the multiple component reference beams to form a composite reference beam;
    applying the probe beam to the target to be analyzed;
    capturing at least part of said probe beam scattered from within the target to form captured scattered probe radiation;
    combining the captured scattered probe radiation and the composite reference beam;

detecting the resulting composite interferometric signal to form a composite electronic signal;

separating the composite electronic signal into signals related to concurrent information from different locations within the target; and processing said concurrent information to achieve non-invasive analysis of the target.

2. The method of claim 1, wherein the probe and reference beams are generated by at least one super-luminescent diode.

3. The method of claim 1, wherein the probe and reference beams are generated by at least one source of broadband radiation.

4. The method of claim 1, wherein the reference beam is separated into component reference beams by at least one beam-splitter.

5. The method of claim 1, wherein the reference beam is separated into component reference beams by a polarization sensitive reflective element.

6. The method of claim 1, wherein the reference beam is separated into component reference beams by a partially reflective element.

7. The method of claim 1, wherein the reference beam is separated into component reference beams by at least one optical fiber coupler.

8. The method of claim 1, wherein the reference beam is separated into component reference beams by a MEMS based mirror array.

9. The method of claim 1, wherein component reference beams are modulated by one or more phase modulators.

10. The method of claim 1, wherein component reference beams are modulated by one or more length modulators.

11. The method of claim 1, wherein different component reference beams are modulated in a manner that results in interferometric signals with different frequency content.

12. The method of claim 11, wherein at least some aspects of the different frequency content are harmonically related.

13. The method of claim 1, wherein the signals related to different component reference beams are separated by electronic processing of the detected composite electronic signal.

14. The method of claim 1, wherein the signals related to the different component reference beams are separated by digital signal processing of the detected composite electronic signal.

15. The method of claim 1, wherein the concurrent information from different locations is processed to provide scattering information.

16. The method of claim 15, wherein the scattering information is analyzed to determine a measurement of an analyte.

17. The method of claim 16, wherein the measurement of an analyte is the concentration level of glucose in tissue.

18. The method of claim 1, wherein the concurrent information from different locations is analyzed to provide imaging information.

19. The method of claim 1, wherein the reference beam is seperated into component reference beams and at least a portion of the component reference beams are re-combined into the coposite reference beam by the combination of at least one partially reflective element and at least one substantially fully reflective element.

20. The method of claim 19, wherein at least one substantially fully reflective element is a modulating reflective element.

21. The method of claim 19, wherein at least one partially reflective element is a modulating reflective element.

22. A system for non-invasive analysis of a target, said system comprising:

a source operable to generate broadband radiation;

a beam splitter operable to separate said broadband radiation into a probe beam and a reference beam;

a partially reflective surface operable to separate said reference beam into multiple component reference beams and operable to re-combine at least part of some of said multiple component reference beams to form a composite reference beam;

a modulating reflective element operable to modulate at least some of said multiple component reference beams;

an optical element operable to apply said probe beam to the target to be analyzed;

a beam splitter operable to combine at least part of said probe beam scattered from within the target with at least part of said composite reference beam;

a detector operable to detect a composite interferometric signal, said composite interferometric signal resulting from detection of at least part of said probe beam scattered from within the target and at least part of said composite reference beam, and operable to form a composite electronic signal; and, a processing module operable to separate said composite electronic signal into signals related to concurrent information from different locations and operable to process said concurrent information to achieve non-invasive analysis of the target.

23. An apparatus for non-invasive analysis of a target, said apparatus comprising:

means for generating a probe beam and a reference beam;

means for separating the reference beam into multiple component reference beams;

means for modulating at least some of the multiple component reference beams;

means for re-combining at least part of some of the multiple component reference beams by at least some of the elements that separated such multiple component reference beams to form a composite reference beam;

means for applying the probe beam to the target to be analyzed;

means for capturing at least part of said probe beam scattered from within the target to form captured scattered probe radiation;

means for combining the captured scattered probe radiation and the composite reference beam;

means for detecting the resulting composite interferometric signal to form a composite electronic signal;

means for separating the composite electronic signal into signals related to concurrent information from different locations; and means for processing said concurrent information, wherein said means for processing said simultaneous information enables non-invasive analysis of the target.

24. The apparatus of claim 23, wherein the probe and reference beams are generated by at least one super-luminescent diode.

25. The apparatus of claim 23, wherein the probe and reference beams are generated by at least one source of broadband radiation.

26. The apparatus of claim 23, wherein the reference beam is separated into component reference beams by at least one beam-splitter.

27. The apparatus of claim 23, wherein the reference beam is separated into component reference beams by a polarization sensitive reflective element.

28. The apparatus of claim 23, wherein the reference beam is separated into component reference beams by a partially reflective element.

29. The apparatus of claim 23, wherein the reference beam is separated into component reference beams by at least one optical fiber coupler.

30. The apparatus of claim 23, wherein the reference beam is separated into component reference beams by a MEMS based mirror array.

31. The apparatus of claim 23, wherein component reference beams are modulated by one or more phase modulators.

32. The apparatus of claim 23, wherein component reference beams are modulated by one or more length modulators.

33. The apparatus of claim 23, wherein different component reference beams are modulated in a manner that results in interferometric signals with different frequency content.

34. The apparatus of claim 33, wherein at least some aspects of the different frequency content are harmonically related.

35. The apparatus of claim 23, wherein the signals related to different component reference beams are separated by electronic processing of the detected composite electronic signal.

36. The apparatus of claim 23, wherein the signals related to the different component reference beams are separated by digital signal processing of the detected composite electronic signal.

37. The apparatus of claim 23, wherein the concurrent information from different locations is processed to provide scattering information.

38. The apparatus of claim 37, wherein the scattering information is analyzed to determine a measurement of an analyte.

39. The apparatus of claim 38, wherein the measurement of an analyte is the concentration level of glucose in tissue.

40. The apparatus of claim 23, wherein the concurrent information from different locations is analyzed to provide imaging information. fully reflective element.

41. The apparatus of claim 23, wherein the reference beam is separated into component reference beams and at least a portion of the component reference beams are re-combined into the composite reference beam by the combination of at least one partially reflective element and at least one substantially fully reflective element.

42. The apparatus of claim 41, wherein at least one substantially fully reflective element is a modulating reflective element.

43. The apparatus of claim 41, wherein at least one partially reflective element is a modulating reflective element.

* * * * *